United States Patent [19]

Wagner et al.

[11] Patent Number: 4,717,676
[45] Date of Patent: Jan. 5, 1988

[54] VESICLES AND USE THEREOF IN AN ASSAY

[75] Inventors: Daniel B. Wagner, Raleigh, N.C.; Uri Piran, Norwood, Mass.

[73] Assignee: Becton Dickinson and Company, Franklin Lakes, N.J.

[21] Appl. No.: 835,781

[22] Filed: Mar. 3, 1986

[51] Int. Cl.$^4$ .......................................... G01N 33/544
[52] U.S. Cl. ................................... 436/501; 436/500; 436/518; 436/528; 436/815; 436/829
[58] Field of Search ............... 436/500, 501, 518, 528, 436/815, 829

[56] References Cited

U.S. PATENT DOCUMENTS 4,483,929 11/1984 Szoka .................................. 436/829

OTHER PUBLICATIONS

R. Neumann et al Chem. Abs. 104, 110158f, 1986.

*Primary Examiner*—Sidney Marantz
*Assistant Examiner*—David A. Saunders
*Attorney, Agent, or Firm*—Elliot M. Olstein

[57] ABSTRACT

Sacs comprising a compound having a hydrophilic peptide radical are prepared and are believed to have improved stability as a result of hydrogen bonding. The sacs, including a detectable marker and derivatized with a ligand may be used as a tracer in an assay.

14 Claims, No Drawings

VESICLES AND USE THEREOF IN AN ASSAY

This invention relates to vesicles and sacs and to the use thereof. This invention further relates to an assay for a ligand which employs a vesicle or sac as a component thereof.

Vesicles or sacs are generally produced from amphiphilic compound (compounds having both a hydrophobic portion and a hydrophilic portion), with such vesicles or sacs being most commonly produced from lipids; in particular, phospholipids. When the vesicles or sacs are produced from lipids they are most often referred to as liposomes.

As known in the art, such vesicles or sacs may be formed in a manner such as to encapsulate a material in the interior of the sac. Thus, for example, such sacs have been used to encapsulate biologically active materials; for example, a therapeutic drug.

In addition, such sacs have been employed to encapsulate a detectable marker for use in an assay for a ligand. Thus, for example, in an assay for a ligand, the tracer used in the assay may be produced by coupling the ligand or appropriate analog thereof to a sac containing a detectable marker. In such an assay, for example, the tracer and ligand to be determined (analyte) may compete for a limited number of bindings sites on a binder for both the tracer and analyte. The amount of tracer which is bound to the binder is inversely proportional to the amount of analyte in the sample. The bound and/or unbound portion of the tracer is determined as a measure of analyte by releasing the marker from the sac.

In such assays, in producing a tracer, it is necessary to conjugate a ligand to the sac containing the detectable marker. It has been found that in many cases such tracers do not have the requisite stability; i.e., after a period of time, the sac deteriorates and/or the ligand does not remain coupled to the sac. In addition, it is necessary to produce and store sacs conjugated to a variety of ligands for use in assays for a variety of analytes.

In accordance with one aspect of the present invention, there is provided an improved sac or vesicle wherein at least a portion of the sac is formed from a compound having the following structural formula I:

$$X-Y-Z \quad (I)$$

wherein
X is a hydrophobic radical;
Y is a hydrophilic peptide; and
Z is a radical which includes a non-hydrolyzable polar group.

The use of a peptide as part of the hydrophilic portion of the compound used in forming the sac increases the stability of the sac. Although applicant does not intend that the invention be limited by any theoretical reasoning, it is belived that the increased stability results from hydrogen bonding between the peptide portions of the compounds forming the wall of the sac.

The hydrophobic radical represented by X may be any one of a wide variety of hydrophobic radicals whih are known to be suitable as the hydrophobic portion of a compound used in producing a sac. As representative examples of suitable hydrophobic radicals, there may be mentioned hydrophobic radicals represented by the following structural formula II and III:

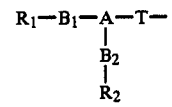

wherein
each of $R_1$ and $R_2$ is a substituted or unsubstituted hydrocarbon radical (saturated or unsaturated) having at least 11 carbon atoms and may be the same or different radicals and $R_1$ and $R_2$ may be linked together to form a cyclic compound, each of $B_1$ and $B_2$ is $-CH_2-$, $-C(O)NH-$, $-NH-$, $-C(O)O-$, $-O-$, $-S-$, and may be the same or different radicals;
T is $-NH-$ or $-R_4-F-$ wherein $R_4$ is a $C_1$ to $C_3$ hydrocarbon and F is $-S-$; $-NH-$, or $-C(O)-$; and
A is a hydrocarbon radical having from 1 to 4 carbon atoms, preferably 3 or 4 carbon atoms.

The peptide represented by Y in the hereinabove described structural formula is a peptide formed from at last two amino acids and the molecular weight is such that the peptide is hydrophilic (if the molecular weight is too high the peptide may become hydrophobic). The amino acids forming the peptide generally do not have more than four carbon atoms; for example, B-alanine, glycine, serine, threonine, etc.

As representative examples of polar groups which are not hydrolyzable, and which in combination with the hydrophilic spacer radical Y are sufficient to produce a sac, there may be mentioned sulfonates, phosphonates, phosphinates and quaternary amines. The polar group may be directly substituted on the terminal amino acid of the peptide or may be connected through a peptide linkage to a spacer radical, which includes the polar head group, with the spacer group being insufficient to change the hydrophilic nature of the peptide.

The peptide employed in producing the compounds used for forming a sac may be synthesized by any one of a variety of procedures for producing a peptide from amino acids. The hydrophobic radical may be linked to the peptide, by standard techniques for peptide synthesis. The precursor comprised of the hydrophobic radical coupled to a peptide may then be treated to provide the peptide portion with a non-hydrolyzable polar group. For example, the peptide may be derivatized with sarcosine and the terminal amino group is then quaternized with propyl sulfonate by procedures known in the art. As another example, the peptide may be derivatized with a sulfo-phenylisothiocyanate by procedures known in the art. These and other procedures should be apparent to those skilled in the art.

The sacs produced in accordance with the present invention may be comprised entirely of one or more compounds of the type hereinabove described, or the sac or vesicle may be comprised of one or more compounds of the type hereinabove described and one or more other compounds suitable for producing sacs. As representative examples of compounds which can be used in addition to those of the type hereinabove described, there may be mentioned: lipids, including phospholipids, glycolipids, steroids, relatively long chain alkyl esters; e.g., alkyl phosphates, fatty acid esters; e.g., lecithin, fatty amines and the like. A mixture of fatty materials may be employed such as a combination of neutral steroid, a charged amphiphilic and a phospholipid. As illustrative examples of phospholipids there may be mentioned sphingomyelin, dipalmitoyl, lecithin, and the like. As representative steroids, there may be mentioned cholesterol, cholestanol, lanosterol, and the like. As representative examples of charged amphiphilic compounds, which generally contain from 12 to 30 carbon atoms, there may be mentioned mono- or dialkyl phosphate ester, quaternary ammonium salts, or an alkylamine; e.g., dicetyl phosphate, stearyl amine, hexadecyl amine, dilauryl phosphate, dioctadecyl sulfonate, didodecyl dioctylammonium formide, and the like. As should be apparent, the best results are obtained when the amount of phospholipid and/or glycolipid used in producing the sac is minimized; i.e., phospholipids are present in amounts less than 10%, preferably less than 5%. Steroids such as cholesterol are advantageously included in forming the sac in that, as known in the art, such steroids provide stability to the sac.

The sacs or vesicles, which have at least a portion of the wall thereof formed from a compound having the hereinabove described structural formula which includes a peptide may be produced by procedures generally available in the art for producing sacs or vesicles. For example, the sac or vesicle may be produced by a reverse phase evaporation technique wherein the compound or compounds used in producing the sac or vesicle are initially dissolved in an organic phase, followed by addition of an aqueous phase and forming of a homogeneous emulsion. After forming the emulsion, the organic solvent is evaporated to form a gel-like material, and such gel may be converted to a sac or vesicle by agitation or dispersion in an aqueous media such as a buffer solution.

Procedures for producing vesicles or sacs are generally known in the art, and such procedures may be employed for producing a sac or vesicle in accordance with the present invention.

Details with respect to the preparation of sacs are set forth in U.S. Pat. Nos. 4,241,046, 3,342,826 and P.C.T. International Publication No. Patent WO 80-01515.

As known in the art, if a material is to be encapsulated in the sac, such material may be encapsulated by including the material in an aqueous solution in which the sac or vesicle is formed. Alternatively, the material may be encapsulated into a previously formed "empty" sac by the procedure described in U.S. application Ser. No. 650,200, filed on Sept. 13, 1984.

The sac or vesicle produced in accordance with the present invention may be derivatized with a ligand and provided with a detectable marker for use as a tracer in an assay for an analyte. Depending on the assay, the ligand may be an antigen, hapten or antibody or a naturally occurring binder or receptor. Thus, for example, if the assay is a competitive assay for determining an antigen or hapten, the ligand employed in producing the tracer is either the analyte or appropriate analog thereof. The term "appropriate annalog" means that the analog of the analyte is bound by the binder for the analyte.

If the assay is a "sandwich" type of assay, then the ligand employed in producing the tracer would be a ligand which is specific for the analyte to be assayed; for example, an antibody elicited in response to the antibody or antigen to be assayed. Alternatively, the antibody could be a monoclonal antibody.

The binder which is used in the assay is also dependent upon the analyte. Thus, for example, if the analyte is an antigen or hapten, the binder may be an antibody (polyclonal or monoclonal) or a naturally occurring substance which is specific for the analyte. If the analyte is an antibody, the binder may be either an antibody, an antigen or naturally occurring substance which is specific for the analyte.

The binder which is used in the assay may be employed in supported or unsupported form.

The detectable marker used in the assay is generally employed in the assay is generally enclosed or encapsulated within the sac or vesicle; however, the vesicle may be derivatized with the marker in a manner similar to derivatizing the sac with a ligand. For example, the sac may be derivatized with the ligand by derivatizing a compound(s) used in forming the wall of the sac with the ligand either before or after forming the sac. The ligand may be coupled to the sac by use of suitable coupling or spacer compounds, or in the case where compound(s) forming the sac and the ligand have appropriate substituent groups, the ligand may be coupled directly to the sac. For example, if one of the ligand or sac has an amino substituent group and the other has a carbonyl or carboxyl substituent group, the ligand and sac may be directly coupled to each other by procedures known in the art. Similar procedures may be used in derivatizing the sac with a detectable marker. In most cases, the detectable marker is encapsulated within the sac.

The detectable marker may be any one of a wide variety of detectable markers, including but not limited to radioisotopes, chromogens (an absorbing dye and/or a fluorescent material), a luminescent compound, spin labels, a detectable metal, etc. Such detectable markers, and the method for determining the markers are generally known in the art, and no further details in this respect are deemed necessary for a complete understanding of the invention. The preferred types of markers are dyes with a high extinction coefficient, such as sulforhodamine B, fluorescent dye such as carboxyfluorescein, and the like.

The assay may be a solid phase assay of a type known in the art wherein the binder is supported on a solid support. As generally known in the art, the use of a solid phase facilitates separation of bound and free portions of the tracer.

As a representative example of an assay procedure in accordance with the present invention, there may be mentioned an assay wherein a sample containing or suspected of containing the analyte is incubated with a tracer, which is the analyte or appropriate analog thereof coupled to a sac of the type hereinabove described which includes a detectable marker, and a binder specific for both the analyte and tracer. The incubation results in competition between the tracer and analyte for binding sites on the binder, with the amount of tracer which is bound to the binder being inversely proportional to the amount of analyte in the sample.

The contact or incubation of the sample, tracer and specific binder is accomplished under conditions which prevent premature rupturing of the sacs. The incubation or assay is generally run in an appropriately buffered aqueous medium which is isotonic with the osmolarity of the sacs. Thus, conditions of temperature, pH and ionic concentration are controlled to prevent premature rupturing of the sacs. Thus, for example, an aqueous buffered medium is provided which is isotonic with the osmolarity of the sacs, with the buffer generally providing a pH in the order of from 5 to 9.

After the incubation, the amount of tracer in the bound and/or free portion is determined from the marker in the sacs. In general, the marker is released from the sac in order to determine the marker; however, in some cases, it may be possible to determine a marker without releasing the marker from the sacs.

The marker may be released from the sacs by rupturing or dissolving the sacs. For example, marker can be released by addition of distilled water (osmotic lysing), enzyme lysing (digesting), the use of solvents (dissolving of microcapsules of polymers), or by application of heat, mechanical pressure, sonication, etc. Such techniques are generally known in the art, and no further details in this respect are deemed necessary for an understanding of the invention.

In general, the bound and/or free portion is determined by separating the bound and free portions by techniques known in the art. Thus, for example, in the case where a solid phase assay is employed (binder support on a solid support), separation of the bound and free portions is easily accomplished. If a soluble binder is employed, bound and free portions may be separated by procedures known in the art; for example, by adsorption or by use of coated charcoal. In some cases, it may be possible to determine the bound and/or free portion without effecting separation thereof.

The rate at which the marker is released into the medium and/or the amount of marker which is released into the medium is dependent upon the concentration of tracer present, with an increasing amount of tracer resulting in an increase in the rate and/or amount of release of marker into the medium. Thus, by determining the rate at which marker is released into the medium, or in the alternative, by determining the amount of marker in the medium after a fixed period of time, and comparing such values with those obtained by an identical procedure using known amounts of analyte (standard analyte having known concentrations), there can be obtained a measurement of the amount of analyte present in the sample.

The rate can be determined either kinetically by measuring the signal intensity increase with time, or by the end point method, where the reaction is allowed to proceed for a fixed length of time and is then stopped (for example, by increasing the pH), and the color (or fluorescent, or luminescence, as the case may be) is measured. The higher the reaction rate, the stronger will be the signal at the end point.

The sample volume which is used in the assay is selected so as to prevent a "runaway" rate for release of the marker; i.e., to provide a detectable rate of change with time and/or a detectable difference in the amount of marker released dependent upon concentration of analyte in the original sample. Thus, as the expected analyte concentration increases, the sample volume may be decreased so as to provide for a detectable change in rate and/or a detectable difference in the amount of analyte in a given sample.

As another procedure, a so-called "sandwich" assay may incorporate a tracer formed from a sac as hereinabove described.

In such an assay, the tracer is comprised of a sac, as hereinabove described, which is derivatized with a binder for the ligand to be determined, such as an antibody; e.g., a monoclonal antibody. The tracer, sample and supported binder, for example, an antibody (monoclonal or polyclonal antibody) are contacted (forward, reverse or simultaneous technique) to produce a complex of ligand to be determined, which is bound to both the supported binder and the tracer, as well as an unbound tracer fraction. The amount of bound tracer is directly proportional to the amount of ligand in the sample.

The tracer in the bound portion or the unbound portion may be determined as hereinabove described to determine ligand in the sample.

The above procedure and others would be apparent to those skilled in the art.

In accordance with a further aspect of the invention, there is provided a reagent kit or package useful in determining a ligand in a sample (analyte) which contains in a suitable reagent package (a) a tracer comprised of a sac of the type hereinabove described derivatized with a ligand which is either the analyte, appropriate analog of the analyte or a binder for the analyte, and which sac further includes a detectable marker and (b) a binder for at least one of the analyte and tracer, in supported or unsupported form, with the binder generally being a binder for the analyte. In a competitive type of assay, the binder is a binder for both the tracer and analyte.

The components of the kit may be included in the kit or package in separate containers; for example, vials; however, in some cases, one or more of the components may be combined into a single vial. The kit may also include other components such as standards of the analyte (analyte samples having known concentrations of the analyte), known buffers, and the like. Such kit or package may be employed in an assay for an analyte by use of procedures of the type hereinabove described.

The assay and reagent kit of the present invention may be employed for determining a wide variety of analytes. As representative examples of such analytes, there may be mentioned: cardiac glycosides, such as digoxin and digitoxin; antiasthmatics, such as theophyllin; antibiotics, such as gentamycin and tobramycin, atineopalastics such as amethotrexate; anticonvulsants, such as pheno-barbital, carbamexapine and valpaaric acid; antiarrythmics, such as lidocaine and quinidine; hormones, such as T4, T3, hCG, TSH, and various steroids. These and other analytes should be apparent to those skilled in the art, and no further teachings in this respect are deemed necessary for a full understanding of the invention. It is to be understood that the scope of the present invention is not to be limited to the representative analytes.

The sample containing the analyte is generally a body fluid, such as serum, sputum, urine, etc.

The present invention will be further described with respect to the following examples; however, the scope of the invention is not to be limited thereby.

EXAMPLE

A. Preparation of B-Alanyl-glycyl-Glycyl-Dioctadecylamide:

N-t-BOC-B-alanyl-glycyl-glycine is prepared by a standard method from N-T-BOC-B-alanine and glycylglycine methyl ester, using the DCC and N-hydroxysuccinimide condensation reaction. The ester is hydrolyzed in dilute base and the peptide is recovered by extraction of the acidified (pH 2) reaction mixture.

Add DCC (4.0 g) to a solution of the above peptide (5.3 g) and N-hydroxysuccinimide (2.0 g) in dry THF. After 90 minutes at room temperature, filter, evaporate the filtrate and re-dissolve the residue in dry THF. Add this solution to a suspension of dioctadecylamine (purified by recrystallization from Hexane) (11.0 g) in methylene chloride. After stirring for eighteen (18) hours, the product is isolated by evaporating the reaction mixture to dryness, extracting with hot hexane and chromatographing this extract on silica-gel, using methylene chloride for elution of the pure product. The t-BOC protecting group is removed by dry HCl in dry dioxane.

B. 2.0 g. of the compound produced in A; 2 g. of 4-sulfophenylisothiocyanate sodium salt and 50 ml. of 10% triethylamine in methanol was stirred at R.T. overnight. The clear solution was evaporated to dryness, the residue was taken up in $CH_2Cl_2$, filtered and the filtrate (approx. 5 ml.) was applied to a silica gel column prepared in 10% MeOH in $CH_2Cl_2$. The major band (strong UV) was eluted with $CH_2Cl_2$:MeOh:$CH_3CO_2H$ 90:9.5:0.5 Yield 1.3 gr. TLC (10% MeOH in $CH_2Cl_2$ plus a trace of $CH_3CO_2H$, silica gel).

C. Molecular sieve (4A ~0.5 gr) was added to a solution of digoxin dialdehyde (prepared by routine periodate oxidation of digoxin) (400 mg) and the long-chain tri-peptide (0.5 gr) (prepared in Example A) in dry MeOH (~10 ml), followed, after ten minutes at room temperature, by sodium cyano borohydride (~50 mg). The reaction mix was kept overnight at room temperature, without stirring.

TCL (silica gel, 10% MeOH in $CH_2Cl_2$): only a trace of the starting digoxin dialdehyde. The reaction mix was filtered (fine filter), evaporated to dryness and the residue was taken up in 10% $CH_2Cl_2$ in hexane, (~40 ml). The cloudy solution was filtered twice through Acrodisc 0.45μ and evaporated to dryness. The white foam was dissolved in $CH_2Cl_2$ (~5 ml). The solution was applied to a silica gel column prepared with 5% MeOH in $CH_2Cl_2$ and eluted with the same solvent. 200 mg. of a white foam were obtained, TLC (silica gel) (10% MeOH in $CH_2Cl_2$): single spot, Rf=0.4.

D. Preparation of Dye-Loaded Sacs:

Dissolve an equimolar mixture of the material from B and cholesterol and 200 ug of the material from C in a 9:1 mixture of chloroform and methanol. Evaporate to dryness. Add a solution of sulforhodamine B in water (0.1M) at 60° C. Sonicate briefly, and wash several times with a buffer solution of the same osmolarity as the encapsulated dye (310 mosm/kg) to prevent osmotic lysis. The vesicles are filtered through 0.4μ. filter. The dye-loaded vesicles thus obtained may be used as a tracer in an assay for digoxin.

The present invention is advantageous in that the sacs have an improved stability. As a result, in the case where the sacs are to be used as a tracer, as hereinabove described, both storage stability and assay stability of the tracer are improved.

Numerous modifications and variations of the present invention are possible in light of the above teachings and, therefore, within the scope of the appended claims, the invention may be practiced otherwise than as particularly described.

What is claimed is:

1. A composition, comprising:
    a sac, said sac including a detectable marker and being derivatized with a ligand, at least a portion of said sac being formed from a compound having the following formula:

X—Y—Z wherein
    X is a hydrophobic radical;
    Y is a hydrophilic peptide; and
    Z is a radical including a non-hydrolyzable polar group.

2. The composition of claim 1 wherein the polar group is sulfonate.

3. The composition of claim 1 wherein the polar group is selected from the group consisting of sulfonate, phosphonate, phosphinate and quaternary amine.

4. In an assay for an analyte wherein at least one of a binder and analyte is contacted with a tracer, the improvement comprising:
    effecting the contacting of at least one of the analyte and binder with a tracer comprising the composition of claim 3 wherein the ligand of the tracer is bound by one of the binder and analyte.

5. A reagent kit for determining an analyte, comprising:
    a package, said package including a binder for at least one of an analyte and a tracer; and a tracer comprising the composition of claim 3.

6. The composition of claim 1 wherein the hydrophobic radical X is a radical selected from the group consisting of radicals having structural formulas Ii and III:

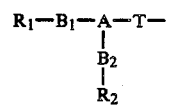

wherein
    each of $R_1$ and $R_2$ is selected from the groups consisting of substituted and unsubstituted hydrocarbon radicals having at least 11 carbon atoms and
    each of $B_1$ and $B_2$ is selected from the group consisting of —$CH_2$—; —C(O)NH—; NH; —C(O)0—; —O—; —S—;
    T is selected from the group consisting of —NH— —$R_4$—F— wherein $R_4$ is a hydrocarbon radical having from 1-3 carbon atoms and F is selected from the group consisting of —S—, —NH—, and —C(O)—, and A is a hydrocarbon radical having from 1 to 4 carbon atoms.

7. In an assay for an analyte wherein at least one of a binder an analyte is contacted with a tracer, the improvement comprising:
    effecting the contacting of at least one of the analyte and binder with a tracer comprising the composition of claim 6 wherein the ligand of the tracer is bound by one of the binder and analyte.

8. A reagent kit for determining an analyte, comprising:
    a package, said package including a binder for at least one of an analyte and a tracer; and a tracer comprising the composition of claim 6.

9. In an assay for an analyte wherein at least one of a binder an analyte is contacted with a tracer, the improvement comprising:

effecting the contacting of at least one of the analyte and binder with a tracer comprising the composition of claim 1, wherein the ligand of the tracer is bound by one of the binder and analyte.

10. The assay of claim 9 wherein the detectable marker is a chromogen.

11. The assay of claim 10 wherein the chromogen is sulforhodamine B.

12. A reagent kit for determining an analyte, comprising:

a package, said package including a binder for at least one of an analyte and a tracer; and a tracer comprising the composition of claim 1.

13. The reagent kit of claim 12 wherein the detectable marker is a chromogen.

14. The reagent kit of claim 13 wherein the chromogen is sulforhodamine B.

* * * * *